(12) United States Patent
Nakayama et al.

(10) Patent No.: US 10,471,179 B2
(45) Date of Patent: Nov. 12, 2019

(54) METHOD OF PRODUCING A FILM CONNECTIVE TISSUE BODY USING A CONNECTIVE TISSUE BODY FORMATION SUBSTRATE

(71) Applicant: National Cerebral and Cardiovascular Center, Osaka (JP)

(72) Inventors: Yasuhide Nakayama, Osaka (JP); Tomonori Oie, Osaka (JP); Takeshi Moriwaki, Osaka (JP)

(73) Assignee: NATIONAL CEREBRAL AND CARDIOVASCULAR CENTER, Osaka (JP)

( * ) Notice: Subject to any disclaimer, the term of this patent is extended or adjusted under 35 U.S.C. 154(b) by 113 days.

(21) Appl. No.: 15/526,062

(22) PCT Filed: Nov. 13, 2015

(86) PCT No.: PCT/JP2015/081964
§ 371 (c)(1),
(2) Date: May 11, 2017

(87) PCT Pub. No.: WO2016/076416
PCT Pub. Date: May 19, 2016

(65) Prior Publication Data
US 2017/0319745 A1    Nov. 9, 2017

(30) Foreign Application Priority Data

Nov. 13, 2014 (JP) ................. 2014-230327

(51) Int. Cl.
| | | |
|---|---|---|
| *A61L 27/36* | (2006.01) | |
| *A61F 2/24* | (2006.01) | |
| *A61F 2/02* | (2006.01) | |
| *A61L 27/38* | (2006.01) | |
| *C07K 14/78* | (2006.01) | |

(52) U.S. Cl.
CPC ............ *A61L 27/3645* (2013.01); *A61F 2/02* (2013.01); *A61F 2/2415* (2013.01); *A61L 27/3804* (2013.01); *A61L 2430/20* (2013.01); *C07K 14/78* (2013.01)

(58) Field of Classification Search
CPC ............... A61F 9/0017; A61F 9/00781; A61F 2250/0067; A61F 2210/0061; A61F 2250/0068; A61F 2250/0001; A61F 2/02; A61F 2/2415; A61K 9/0051; A61K 9/0092; A61K 31/5575; A61K 9/2072; A61K 35/12; A61K 47/02; A61K 47/32; A61K 9/0048; A61K 41/0028; C12M 21/08; C12M 25/14; C12N 2501/13; C12N 2502/08; C12N 2502/99; C12N 2533/10; C12N 2533/30; C12N 2533/32; C12N 2533/50; C12N 2533/52; C12N 2535/10; C12N 5/0068; C12N 5/0618; A01N 1/0284; A61L 2430/20; A61L 27/3645; A61L 27/3804; B01L 7/50; C07K 14/78; G01N 33/5061; G01N 33/566

See application file for complete search history.

(56) References Cited

U.S. PATENT DOCUMENTS

| | | | | |
|---|---|---|---|---|
| 9,956,074 | B2 * | 5/2018 | Nakayama | ................. A61F 2/07 |
| 2003/0059933 | A1 * | 3/2003 | Tresco | ................... C12M 21/08 |
| | | | | 435/299.1 |
| 2006/0140918 | A1 * | 6/2006 | Tresco | ................... C12M 21/08 |
| | | | | 424/93.7 |
| 2014/0163664 | A1 * | 6/2014 | Goldsmith | ....... A61B 17/00491 |
| | | | | 623/1.11 |
| 2016/0051806 | A1 * | 2/2016 | Goldsmith | ............... A61N 1/00 |
| | | | | 604/21 |

FOREIGN PATENT DOCUMENTS

| | | |
|---|---|---|
| JP | 2007-312821 | 12/2007 |
| JP | 2008-237896 | 10/2008 |
| JP | 2010-94476 | 4/2010 |
| JP | 2012-135406 | 7/2012 |
| JP | 2013-90696 | 5/2013 |
| JP | 2013-240306 | 12/2013 |
| JP | 2014-30598 | 2/2014 |

OTHER PUBLICATIONS

International Search Report dated Jan. 24, 2016 in International (PCT) Application No. PCT/JP2015/081964.

* cited by examiner

*Primary Examiner* — Deborah K Ware
(74) *Attorney, Agent, or Firm* — Wenderoth, Lind & Ponack, L.L.P.

(57) ABSTRACT

The present invention provides a connective tissue body formation substrate which can form a film connective tissue having a desired thickness and both surfaces in a desired surface condition without prolonging the time required for formation of the connective tissue. Specifically, two tissue formation surfaces 2a and 2b are faced with each other with a tissue formation space 3 being interposed therebetween. A slit 9 is formed in the tissue formation surface 2b so that the tissue formation space 3 communicates with an outside of the substrate. A connective tissue body formation substrate 1 is installed in an environment where a biological tissue material is present. A connective tissue intrudes into the tissue formation space 3 from the slit 9. Both surfaces of the film connective tissue are formed so as to match the substrate surface.

13 Claims, 14 Drawing Sheets

METHOD OF PRODUCING A FILM CONNECTIVE TISSUE BODY USING A CONNECTIVE TISSUE BODY FORMATION SUBSTRATE

TECHNICAL FIELD

The present invention relates to a connective tissue body formation substrate for forming an artificial film connective tissue body and a substrate removal tool.

BACKGROUND ART

Many studies have been made on regenerative medicine which regenerates cells, tissues, and organs lost due to diseases or accidents by artificial materials or cells.

Normally, a body has a self-protection function, and when a foreign substance such as a prickle intrudes into a shallow position in the body, this substance is to be pushed out of the body. It is also known that, when a foreign substance intrudes into a deep position in the body, fibroblasts gradually gather around it and form a capsule of connective tissue mainly made of the fibroblasts and collagen so as to cover the foreign substance and to isolate the foreign substance in the body. As technologies for forming a biological origin tissue from living cells by using a self-protection reaction of the latter, several technologies for forming a connective tissue body by implanting a substrate as a foreign substance in a living body have been reported (see Patent Literatures 1 to 3).

Moreover, Patent Literature 4 discloses a substrate which forms a film connective tissue body having a desired thickness and both surfaces in a desired surface condition by forming a connective tissue between two connective tissue formation surfaces facing each other by arranging a substrate in a living body or the like.

CITATION LIST

Patent Literature

Patent Literature 1: Japanese Patent Laid-Open No. 2007-312821
Patent Literature 2: Japanese Patent Laid-Open No. 2008-237896
Patent Literature 3: Japanese Patent Laid-Open No. 2010-094476
Patent Literature 4: Japanese Patent Laid-Open No. 2014-030598 (paragraphs 0008 and 0009)

SUMMARY OF INVENTION

Technical Problem

However, since the substrate described in Patent Literature 4 is formed so as to intrude a connective tissue between two connective tissue formation surfaces from end portions, the larger the substrate becomes, the longer a length for which the connective tissue should intrude becomes, and there is a concern that time required for formation of the film connective tissue becomes longer.

The present invention has an object to provide a connective tissue formation substrate and a substrate removal tool which can form a film connective tissue body having a desired thickness and both surfaces in a desired surface condition without prolonging the time required for formation of the connective tissue body.

Solution to Problem

In order to achieve the aforementioned object, the connective tissue body formation substrate according to the present invention can form a film connective tissue body on a substrate surface by being installed in an environment where a biological tissue material is present, and two tissue formation surfaces where the connective tissue is formed are provided by facing each other with a tissue formation space interposed therebetween so as to form both surfaces of the film connective tissue body matching a substrate surface, and a slit allowing the tissue formation space and an outside of the substrate to communicate with each other is formed at least in one of the tissue formation surfaces.

According to the aforementioned constitution, since the two tissue formation surfaces are faced with each other with the tissue formation space interposed therebetween, a film connective tissue body having a desired thickness can be formed by setting its interval as appropriate. Moreover, since both surfaces of the film connective tissue body are formed matching the substrate surface, both surfaces of the connective tissue can be formed having a desired surface condition such that both surfaces of the connective tissue body are formed having smooth surfaces by forming the tissue formation surfaces into the smooth surfaces. Moreover, since the connective tissue body is formed between the two tissue formation surfaces faced with each other, a distance from the tissue formation surface in the connective tissue body to the farthest portion can be made shorter than that in a case where the connective tissue body is formed on an outer side of one surface of the tissue formation surface, and the connective tissue which is thick and has uniform density can be formed.

Moreover, since a slit allowing the tissue formation space and the outside of the substrate to communicate with each other is formed in at least one of the tissue formation surfaces, the connective tissue can be made to intrude into the tissue formation space from the slit in addition to intrusion of the connective tissue from an end portion thereof, or the connective tissue can be made to intrude only from the slit. As a result, time required for forming the connective tissue body in the tissue formation space can be reduced, and moreover, the connective tissue formed in the slit constitutes a rib protruding from the film connective tissue body and functions as a reinforcing section for reinforcing the film connective tissue body.

Here, the "connective tissue" is usually a tissue having collagen as a main component and refers to a tissue formed in a living body, but in description of this Description and claims, it is a concept including a tissue when the tissue corresponding to the connective tissue formed in a living body is formed under an environment outside the living body.

Moreover, the "biological tissue material" refers to a substance required for forming a desired biological origin tissue and includes zooblasts such as fibroblasts, smooth muscle cells, endothelial cells, stem cells, ES cells and iPS cells, various proteins (collagen, elastin), saccharides such as hyaluronic acid and other various physiologically active substances present in living bodies such as cell growth factors and cytokine. This "biological tissue material" includes those originated from mammals such as humans, dogs, cows, pigs, goats, and sheep, birds, fish and other animals or artificial materials equal to them.

Moreover, the "environment where a biological tissue material is present" refers to an inside of a living body (subcutaneously in limbs, shoulders, backs or bellies or implanted in an abdominal cavity, for example) of animals (mammals such as humans, dogs, cows, pigs, goats, and sheep, birds, fish and other animals) or an inside of an artificial environment containing biological tissue materials outside the living body of the animal.

In description of this Description and claims, the slit refers to the one having a slit length larger than twice of a slit width, and the one having a slit length three times larger than the slit width is preferable. The slit is set to such a slit width that can allow easy intrusion of the connective tissue, and a slit length is set to twice or more and preferably three times or more thereof, but an upper limit of the slit length is determined by a size and strength of the substrate.

Regarding the slit, since its slit length is sufficiently longer than the slit width, early closure of the slit by the connective tissue formed on a peripheral edge portion can be prevented by setting the slit width small while a remaining area of the tissue formation surface is sufficiently ensured, and the connective tissue can be easily made to intrude into the tissue formation space.

That is, formation of a circular small hole in the tissue formation surface, for example, can be considered instead of the slit, but in this case, since the connective tissue is formed on the peripheral edge portion of the circular hole, the circular hole is closed from all the directions by the connective tissue itself formed on the whole circumference of the peripheral edge portion, and there is a concern that it interferes with intrusion of the connective tissue into the tissue formation space. On the other hand, when the slit is formed in the tissue formation surface, too, the connective tissue is formed on its peripheral edge portion, but since the connective tissue formed on a slit end portion does not go out to a portion away from the slit end portion, early closure of the entire slit can be prevented, and the connective tissue can be easily made to intrude into the tissue formation space.

More specifically, considering a case where a slit with a slit length approximately twice of a slit width is divided into two parts in a length direction, the connective tissue to intrude into the tissue formation space from each divided portion is prevented from intruding by one of the slit end portions but is not prevented by the other slit end portion. Moreover, considering a case where a slit with a slit length approximately three times of a slit width is divided into three parts in a length direction, the connective tissue to intrude into the tissue formation space from a divided portion at a center is not prevented from intruding by any of the slit end portions.

As described above, since the slit is formed in the tissue formation surface and the connective tissue is made to intrude into the tissue formation space, the connective tissue is easily made to intrude into the tissue formation space, while an area of an intrusion port can be made smaller than a case of formation of a circular hole as the intrusion port of the connective tissue and other cases.

As a result, a ratio of an area of the slit to the tissue formation surface, for example, can be set to ½ or less.

According to this constitution, in the tissue formation surface, an area of a remaining portion having an original function as the tissue formation surface can be made larger than an area of the slit for allowing the connective tissue to intrude into the tissue formation space and thus, both surfaces of the connective tissue can be formed having a desired surface condition, and a connective tissue body which is thick and has a uniform density can be formed.

The connective tissue body formation substrate of the present invention is not particularly limited in a shape of its tissue formation surface or a structure of the entire substrate as long as the two tissue formation surfaces are provided by facing each other and a slit is formed in at least one of them, and various substrates can be employed in accordance with a shape of the connective tissue body to be formed.

For example, such a connective tissue formation body substrate for forming a cylindrical connective tissue body can be exemplified in which a central substrate having the tissue formation surface set to an outer peripheral surface and a cylindrical substrate surrounding this central substrate and having the tissue formation surface set to an inner peripheral surface are provided, and a slit is formed in the cylindrical substrate.

According to this constitution, since the cylindrical substrate surrounds the central substrate, the connective tissue can be easily made to intrude from the slit formed in the cylindrical substrate on the outer side so that the cylindrical connective tissue body can be formed in a space between the central substrate and the cylindrical substrate.

Moreover, at least the outer peripheral surface of the central substrate may be formed of a polymer material, and at least a surface of the cylindrical substrate may be formed of a metal material.

According to this constitution, since the outer peripheral surface of the central substrate is formed of a polymer material having appropriate biocompatibility and inflammatory property, formation of the connective tissue in the tissue formation space can be promoted. Moreover, since the surface of the cylindrical substrate is formed of a metal material on which the connective tissue is not formed relatively easily, early closure of the slit formed in the cylindrical substrate by the connective tissue can be prevented.

Moreover, the slit may be arranged with its longitudinal direction toward a direction in parallel with a substrate center axis.

According to this constitution, the connective tissue can be made to intrude into the slit, and on a surface of the cylindrical connective tissue body, a rib in parallel with its center axis can be formed. As a result, when the cylindrical connective tissue body is to be implanted as an artificial blood vessel or the like, for example, the rib on its surface can be used as a mark for alignment, and twisting of the artificial blood vessel or the like and closure of its inside in implanting can be prevented.

Moreover, the slit may be arranged with its longitudinal direction toward a direction along a spiral around the substrate center axis.

According to this constitution, the connective tissue is made to intrude into the slit and the spiral rib can be formed on the surface of the cylindrical connective tissue body. As a result, when the cylindrical connective tissue body is to be implanted as an artificial blood vessel or the like, for example, the rib on its surface can be used as a mark for alignment, and in a point of the spiral structure, a cylindrical connective tissue body similar to a natural blood vessel or the like constituted by a spiral fiber can be obtained.

Moreover, it is not always necessary to form one cylindrical connective tissue by using one connective tissue body formation substrate, and a plurality of cylindrical connective tissue bodies can be formed at the same time by using one connective tissue body formation substrate.

For example, such a connective tissue body formation substrate for forming a plurality of the cylindrical connective tissue bodies at the same time can be exemplified in which a plurality of central substrates each having the tissue formation surface set to the outer peripheral surface and an accommodating substrate having a plurality of accommodating sections each accommodating this central substrate and having the tissue formation surface set to the inner peripheral surface are provided, and a slit is formed in the accommodating substrate.

According to this constitution, since the inner peripheral surfaces of the plurality of accommodating sections surround the central substrate, respectively, a plurality of the cylindrical connective tissue bodies can be formed on each of the central substrates and the inner surface of each of the accommodating sections at the same time by making the connective tissue intrude from the slit. As a result, the number of times of installation and removal of the substrate required for formation of the plurality of cylindrical connective tissue bodies can be reduced, and a burden on the environment where the substrate is installed can be lightened. Moreover, since a substrate is set to have a size that the plurality of cylindrical connective tissue bodies are formed at the same time, the substrate in the environment can be easily found and removal of the substrate from the environment can be further facilitated.

Moreover, at least the outer peripheral surface of the central substrate may be formed of a polymer material, and at least a surface of the accommodating substrate may be formed of a metal material.

According to this constitution, since the outer peripheral surface of the central substrate is formed of a polymer material having appropriate biocompatibility and inflammatory property, formation of the connective tissue in the tissue formation space can be promoted. Moreover, since the surface of the accommodating substrate is formed of a metal material on which the connective tissue is not formed relatively easily, early closure of the slit formed in the accommodating substrate by the connective tissue can be prevented.

Moreover, such a connective tissue body formation substrate for forming the connective tissue body as an artificial valve can be exemplified in which the central substrate having the tissue formation surface set to the outer peripheral surface and the outer substrate arranged around this central substrate and having a plurality of valve leaf formation sections each having the tissue formation surface set to an inner surface are provided, and a slit is formed in the valve leaf formation section of the outer substrate.

According to this constitution, a valve leaf is formed on a portion covered by the valve leaf formation section in the outer peripheral surface of the center substrate, and an artificial valve body can be formed on a remaining exposed portion and moreover, since a slit is formed in the valve leaf formation section, the valve leaf repeatedly deformed upon receipt of a pressure of a fluid can be easily formed having a desired thickness and surface condition and uniform density.

Moreover, at least the outer peripheral surface of the central substrate may be formed of a polymer material, and at least a surface of the valve leaf formation section may be formed of a metal material.

According to this constitution, since the outer peripheral surface of the central substrate is formed of a polymer material having appropriate biocompatibility and inflammatory property, formation of the connective tissue in the tissue formation space can be promoted. Moreover, since the surface of the valve leaf formation section is formed of a metal material on which the connective tissue is not formed relatively easily, early closure of the slit formed in the valve leaf formation section by the connective tissue can be prevented.

Moreover, a reinforcing material for reinforcing the connective tissue body may be arranged on an outer side of an exposed portion excluding a portion covered by the valve leaf formation section in the outer peripheral surface of the central substrate.

According to this constitution, since the reinforcing material is arranged on the outer side of the exposed portion excluding the portion covered by the valve leaf formation section, only a portion where deformation is not generated such as a valve leaf in the artificial valve can be reinforced by the reinforcing material. Moreover, since the exposed portion on which the reinforcing material is arranged has its tissue formation surface as one plane, formation of the connective tissue is not interfered by presence of the reinforcing material.

Moreover, such a connective tissue formation body substrate for forming a plate-shaped connective tissue body can be exemplified in which two plate-shaped substrates each having a tissue formation surface are provided at an interval from each other, and a slit is formed at least in one of the two plate-shaped substrates.

According to this constitution, since the two plate-shaped substrates each having the tissue formation surface are provided at an interval from each other, the plate-shaped connective tissue body can be formed in a space between the plate-shaped substrates by making the connective tissue to easily intrude from the slit formed in the plate-shaped substrate.

Moreover, a slit may be formed only in one of the two plate-shaped substrates, at least a surface of the plate-shaped substrate not having the slit is formed of a polymer material, and at least the surface of the plate-shaped substrate having the slit may be formed of a metal material.

According to this constitution, since the surface of the plate-shaped substrate not having the slit is formed of a polymer material having appropriate biocompatibility and inflammatory property, formation of the connective tissue in the tissue formation space can be promoted. Moreover, since the surface of the plate-shaped substrate having the slit is formed of a metal material on which the connective tissue is not formed relatively easily, early closure of the slit formed in the plate-shaped substrate by the connective tissue can be prevented.

Moreover, the present invention provides a method of producing a film connective tissue body by using the aforementioned connective tissue body formation substrate.

That is, the method of producing a film connective tissue body according to the present invention includes an installing process of installing a connective tissue body formation substrate in an environment where a biological tissue material is present, a forming process of forming a connective tissue in a tissue formation space while the connective tissue is formed around the connective tissue body formation substrate, a removing process of removing the connective tissue body formation substrate from the aforementioned environment, and a separating process of peeling the connective tissue in the tissue formation space off the tissue formation surface and removing it as a film connective tissue body. Moreover, in the removing process, the connective tissue body formation substrate is fixed, and the connective tissue in a periphery is cut out along an outer surface of the connective tissue body formation substrate and then, the connective tissue body formation substrate is removed.

According to this constitution, the same effect as an effect obtained by employing the constitution of the aforementioned connective tissue body formation substrate can be obtained. Moreover, in the forming process, the film connective tissue body in the tissue formation space inside the substrate is formed integrally with the connective tissue outside the substrate through the slit, but since the connective tissue around the substrate is cut out in the removing process, the substrate and the film connective tissue body can be cut out from the connective tissue outside the substrate, and the substrate can be removed from the environment. Moreover, since the connective tissue in the periphery is cut out along the outer surface of the connective tissue body formation substrate, a rib can be constituted on a surface of the film connective tissue body by the connective tissue remaining in the slit.

The film connective tissue body produced by the method of the present invention is used as a cylindrical film tissue, an artificial valve or a planar film tissue covering a surface layer or functioning in a film state and can be anything such as a blood vessel, a digestive tube, an air tube, a squama, a pericardium, a dura mater, skin, a cornea and the like. Moreover, the film connective tissue body produced by the method of the present invention may be any one of autologous transplantation, homoplastic transplantation, and heteroplastic transplantation to a target of transplantation, but from a viewpoint of avoidance of rejection, autologous transplantation or homoplastic transplantation is preferable as much as possible. Moreover, in the case of heteroplastic transplantation, immune source removal treatment such as well-known decellularization treatment is preferably applied in order to avoid rejection.

Moreover, the present invention provides a substrate removal tool for removing the substrate installed in an environment where a biological tissue material is present and on which a film connective tissue body is formed on a substrate surface from the environment.

Specifically, the substrate removal tool according to the present invention includes an attached section provided on the substrate, a fixing rod for fixing the substrate from outside the environment by being attached to this attached section, and a cutting blade for cutting the connective tissue around the substrate and guides the cutting blade by the fixing rod and performs cutting of the connective tissue.

According to this constitution, the substrate can be fixed from outside the environment by attaching the fixing rod to the attached section of the substrate, and moreover, the fixing rod is also used as a guiding member for guiding the cutting blade and cutting the connective tissue around the substrate and thus, the connective tissue can be easily cut out at an accurate position with respect to the substrate. Therefore, in a case where the film connective tissue body is to be formed on an outer surface of the substrate, the film connective tissue body can be cut out to a predetermined thickness and removed.

Moreover, a tissue formation space into which the connective tissue is to be made to intrude may be provided inside the substrate, and a communication hole allowing this tissue formation space and an outside of the substrate to communicate with each other may be formed.

According to this constitution, since the tissue formation space inside the substrate is made to communicate with the outside of the substrate through the communication hole, the film connective tissue body formed in the tissue formation space is integrated with the connective tissue outside the substrate through the connective tissue in the communication hole, but by cutting out the connective tissue around the substrate by the cutting blade, the substrate and the film connective tissue body can be separated from the connective tissue outside the substrate.

Moreover, when the tissue formation space and the communication hole are to be provided in the substrate, the cutting blade may be a cylindrical blade slidable along the outer peripheral surface of the substrate.

According to this constitution, since the cylindrical blade can be made to slide along the outer peripheral surface of the substrate, the substrate itself can be also used as a guiding member of the cylindrical blade, and moreover, all the connective tissues around the substrate can be removed by leaving the connective tissue in the communication hole.

Moreover, a stopper for regulating movement of the cutting blade may be provided in the substrate, and a mark indicating a cutting amount may be provided in the cutting blade.

According to these constitutions, when the connective tissue around the substrate is to be cut out by the cutting blade, excessive cutting of the connective tissue beyond the substrate can be prevented.

Advantageous Effect of Invention

As described above, according to the present invention, since the two tissue formation surfaces are faced with each other with the tissue formation space interposed therebetween, the film connective tissue body having a desired thickness and surface condition can be formed. Moreover, since the slit is formed in at least one of the tissue formation surfaces, the connective tissue can be made to intrude into the tissue formation space from the slit, and time required for formation of the connective tissue body can be reduced.

DESCRIPTION OF EMBODIMENTS

First to fourth embodiments of a connective tissue body formation substrate and a substrate removal tool according to the present invention will be described below by using the attached drawings.

First Embodiment

Figure 1:
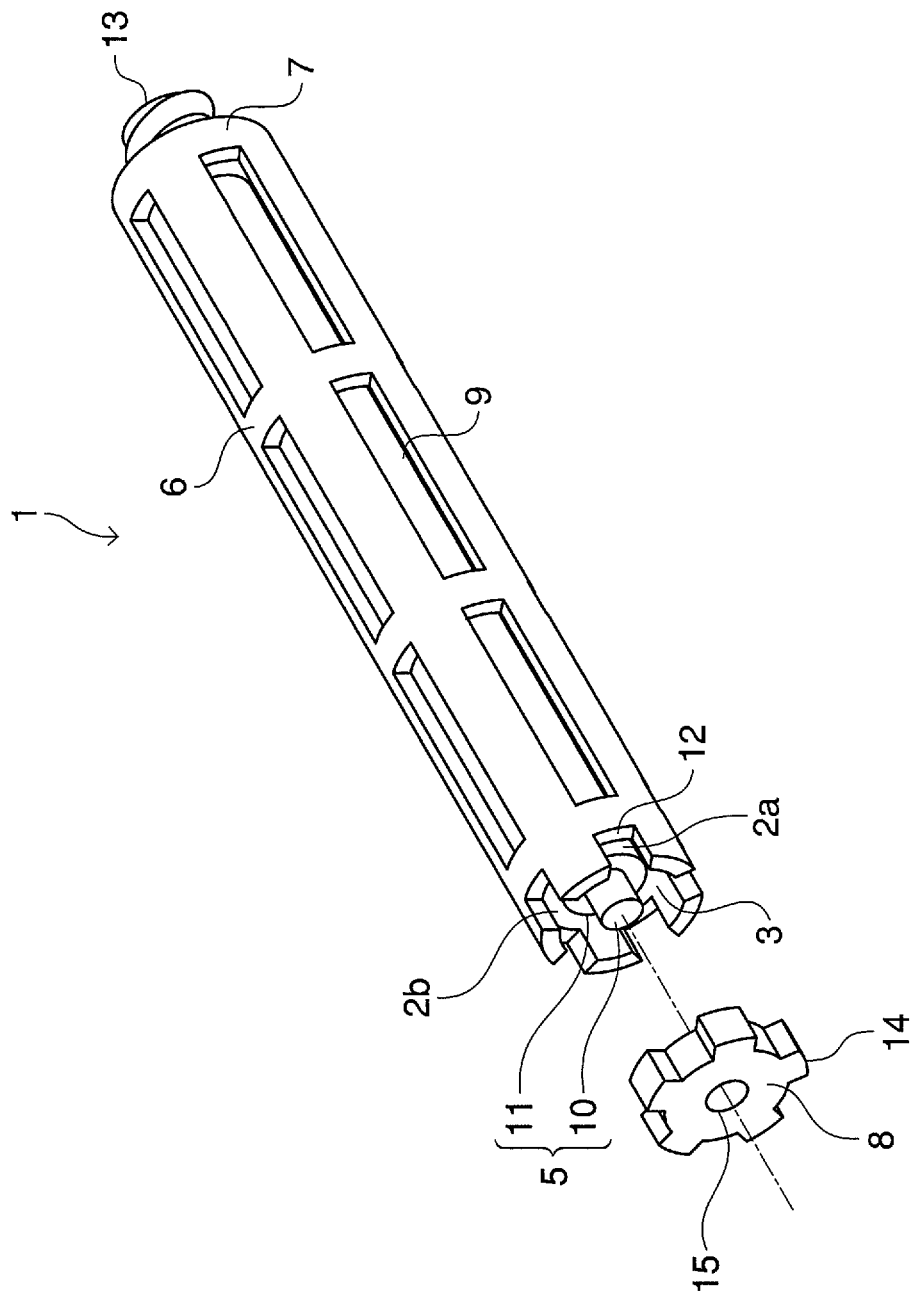
FIG. 1 is a perspective view of a connective tissue body formation substrate according to the present invention (first embodiment).

As illustrated in FIG. 1, a connective tissue body formation substrate 1 is installed in an environment where a biological tissue material is present for forming a cylindrical connective tissue body 4 as a film connective tissue in a cylindrical tissue formation space 3 interposed between two tissue formation surfaces 2a and 2b faced oppositely in the radial direction and includes a central substrate 5 having the tissue formation surface 2a set to an outer peripheral surface, a cylindrical substrate 6 surrounding the central substrate 5 and having the tissue formation surface 2b set to an inner peripheral surface, an end plate 7 closing an end portion of the tissue formation space 3, and a cover plate 8, and a slit 9 allowing the tissue formation space 3 and an outside of the substrate to communicate with each other is formed in the cylindrical substrate 6.

The central substrate 5 has a structure in which a periphery of a central material 10 made of an acrylic resin, for example, is covered by a cover tube 11 made of a silicone resin, for example, and an outer peripheral surface of the cover tube 11 is set to the tissue formation surface 2a. The central material 10 is formed so as to protrude from a center of the end plate 7 toward one surface side, and by setting the cover tube 11 slightly shorter than this central material 10, a distal end of the central material 10 is exposed.

The cylindrical substrate 6 has substantially the same length as that of the central material 10 of the central substrate 5 and has a cylindrical shape made of an acrylic resin, for example, and is formed so as to protrude to the same direction as the central substrate 5 from an outer peripheral edge of the end plate 7 and to surround a periphery of the central substrate 5. At a distal end of this cylindrical substrate 6, a plurality of notches 12 are formed by matching circumferential positions with the slits 9 so as to lock the cover plate 8.

Regarding the central substrate 5 and the cylindrical substrate 6, an outer diameter of the central substrate 5, an inner diameter of the cylindrical substrate 6, and lengths of the central substrate 5 and the cylindrical substrate 6 are set so that the tissue formation space 3 between the tissue formation surfaces 2a and 2b constitutes a predetermined shape in accordance with a width, a thickness, and a length of the intended cylindrical connective tissue body 4.

The end plate 7 has a disk shape made of an acrylic resin, for example, and closes an end portion of the tissue formation space 3, and the central material 10 of the central substrate 5 and the cylindrical substrate 6 are formed integrally through this end plate 7. On a surface in the end plate 7 on a side opposite to the central substrate 5 and the cylindrical substrate 6, an attached section 13 made by providing a screw section is formed so that the connective tissue body formation substrate 1 can be operated from an outside of the environment.

The cover plate 8 has a disk shape made of an acrylic resin, for example, and projecting sections 14 are formed on its peripheral edge, and a small hole 15 is formed at a center of the cover plate 8. This cover plate 8 is attached to the end portion of the cylindrical substrate 6 and closes the end portion of the tissue formation space 3 by engaging the projecting sections 14 with the notches 12 at the distal end of the cylindrical substrate 6 and by fitting an exposed portion at the distal end of the central material 10 into the small hole 15.

A size of the cover plate 8 is set larger than the outer diameter of the cylindrical substrate 6 at a position of the projecting sections 14 and is set larger than the inner diameter of the cylindrical substrate 6 at the other positions. As a result, the cover plate 8 functions as a stopper for regulating movement of a cutting blade when the connective tissue around the cylindrical substrate 6 is cut out.

The slit 9 is set to have a slit width of 0.1 mm or more into which the connective tissue can intrude, for example, and to have a slit length twice or more of this slit width, and the slits are arranged in a plurality of rows in a circumferential direction and in a length direction of the cylindrical substrate 6 with a longitudinal direction toward a direction in parallel with a substrate center axis. The slits 9 have a ratio of an area set to ½ or less with respect to the tissue formation surface 2b of the cylindrical substrate 6, and in the tissue formation surface 2b, an area of a remaining portion forming the outer surface of the cylindrical connective tissue body 4 is set larger than the slits 9 allowing intrusion of the connective tissue.

Here, as a material of the connective tissue body formation substrate 1, a resin which has strength (hardness) that is not largely deformed when being implanted into a living body, chemical stability, resistance against a load such as disinfection and has no or little effluent which stimulates a living body is preferable, and a silicone resin, an acrylic resin and the like as described above can be cited, for example, but it is not limiting.

For example, as described above, at least an outer peripheral surface of the central substrate 5 can be formed by a polymer material such as a silicone resin on which the connective tissue can be formed relatively easily and then, at least a surface of the cylindrical substrate 6 can be formed by a metal material on which the connective tissue is not formed relatively easily. As a result, closure of the slit 9 by the connective tissue can be delayed while the connective tissue is formed in the tissue formation space 3. As a metal constituting the surface of the cylindrical substrate 6, metal which does not rust easily is employed, and metal materials such as stainless, titanium, cobalt, chromium, nickel titanium alloy and the like can be exemplified.

Figure 2:
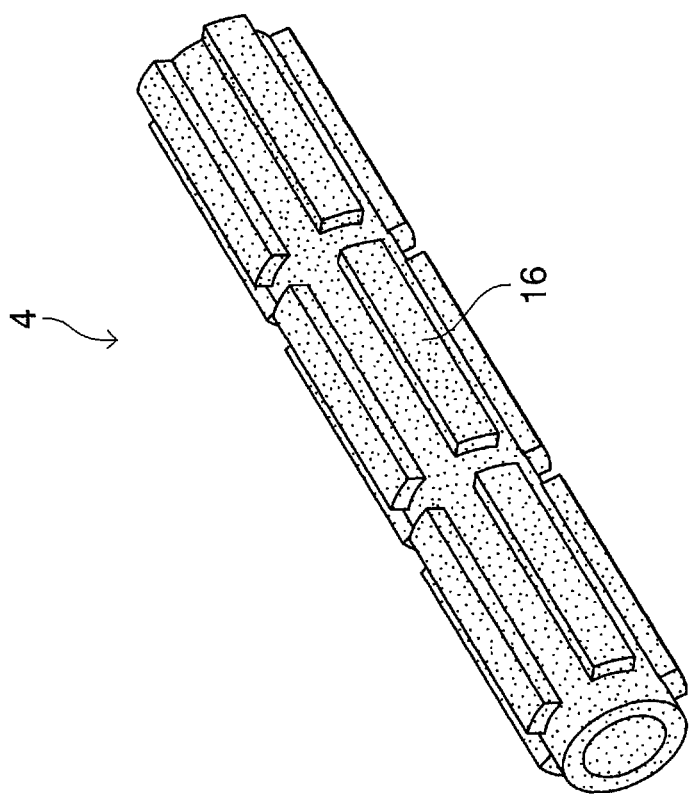
FIG. 2 is a perspective view of a cylindrical connective tissue body.

As illustrated in FIG. 2, the cylindrical connective tissue body 4 produced by using the connective tissue body formation substrate 1 is used as an artificial blood vessel, for example, and a plurality of ribs 16 are formed at portions corresponding to the slits 9.

This cylindrical connective tissue body 4 is constituted as a highly dense and uniform connective tissue having a predetermined thickness and a smooth surface by forming both inner and outer surfaces matching the tissue formation surfaces 2a and 2b. Moreover, since the ribs 16 reinforce the cylindrical connective tissue body 4 and work as marks for alignment in transplantation, twisting which can easily occur in transplantation can be prevented, and closure of the inside caused by twisting of a cylindrical shape can be prevented.

Subsequently, a method of producing the cylindrical connective tissue body 4 by using the connective tissue body formation substrate 1 described above will be described.

Figure 3:
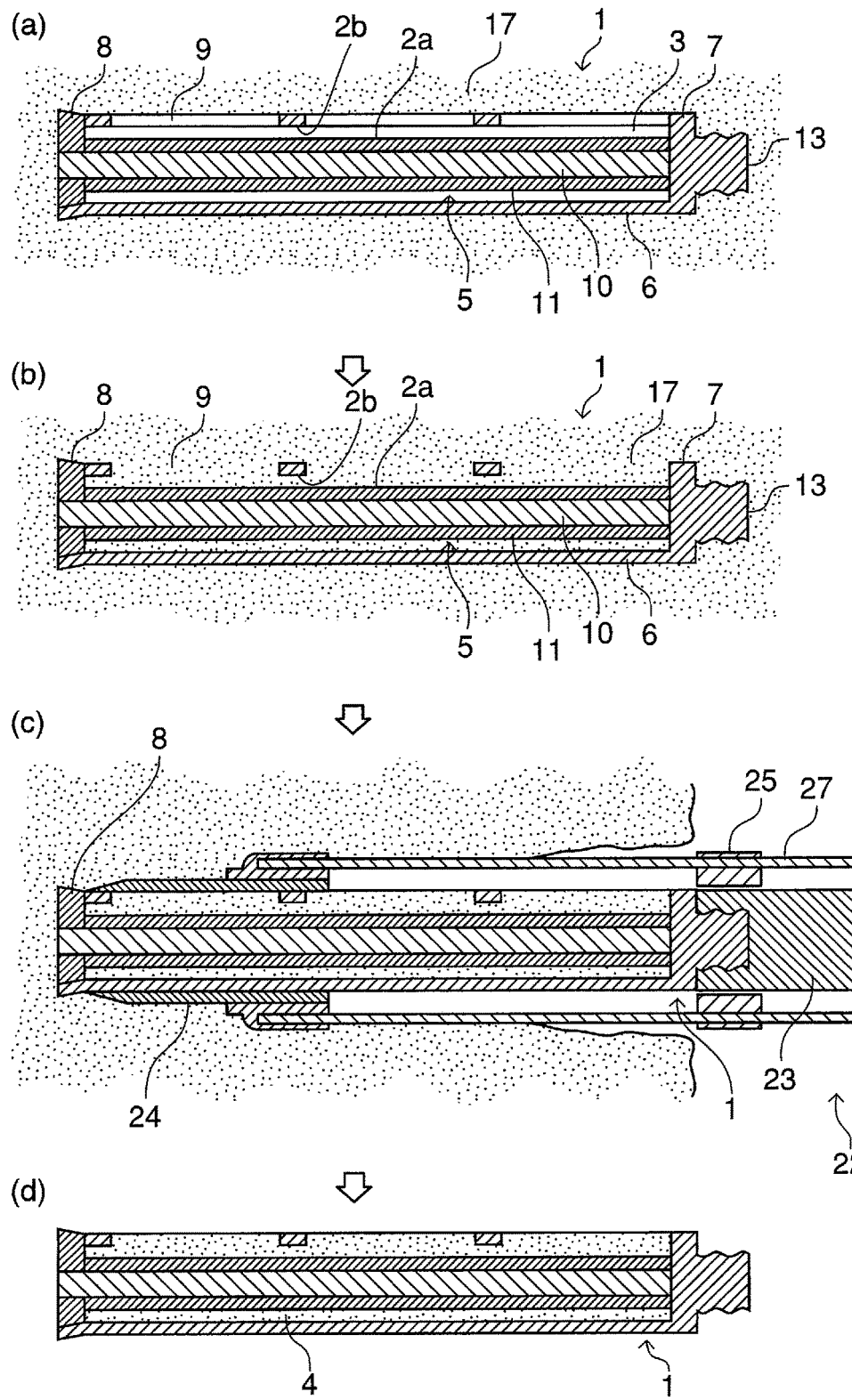
FIG. 3 is a view illustrating a procedure of producing the cylindrical connective tissue body.

As illustrated in FIG. 3, this producing method includes an "installing process" of installing the connective tissue body formation substrate 1 in an environment where a biological tissue material is present, a "forming process" of forming connective tissue 17 in the tissue formation space 3 while the connective tissue 17 are formed around the connective tissue body formation substrate 1, a "removing process" of removing the connective tissue body formation substrate 1 from the environment, and a "separating process" of peeling the connective tissue 17 in the tissue formation space 3 off the tissue formation surfaces 2a and 2b and removing it as the cylindrical connective tissue body 4.

<Installing Process>

The connective tissue body formation substrate 1 is installed in an environment where a biological tissue material is present (FIG. 3(*a*)). The environment where the biological tissue material is present includes an inside of a living body (subcutaneously or implanted into an abdominal cavity, for example) of an animal or an inside of an artificial environment such as in a solution or the like in which the biological tissue materials are floating outside the living body of the animals. As the biological tissue materials, those originated from mammals such as humans, dogs, cows, pigs, goats, rabbits and sheep, birds, fish and other animals or artificial materials can be also used.

When the connective tissue body formation substrate 1 is to be implanted in an animal, it is performed under sufficient anesthesia by minimum incision, and a wound is sutured after the implantation. An implantation portion of the connective tissue body formation substrate 1 is preferably an inside of an abdominal cavity having a capacity for receiving the connective tissue body formation substrate 1 or a subcutaneous portion in limbs, shoulders, backs or bellies, for example. Moreover, for implantation, it is preferably performed with a low-invasive method, and respecting spirit of animal protection, under sufficient anesthesia by minimum incision.

Moreover, when the connective tissue body formation substrate 1 is placed under the environment where the biological tissue material is present, it is only necessary to perform cell culture in accordance with a well-known method under a clean environment by preparing various culture conditions in order.

Figure 4:
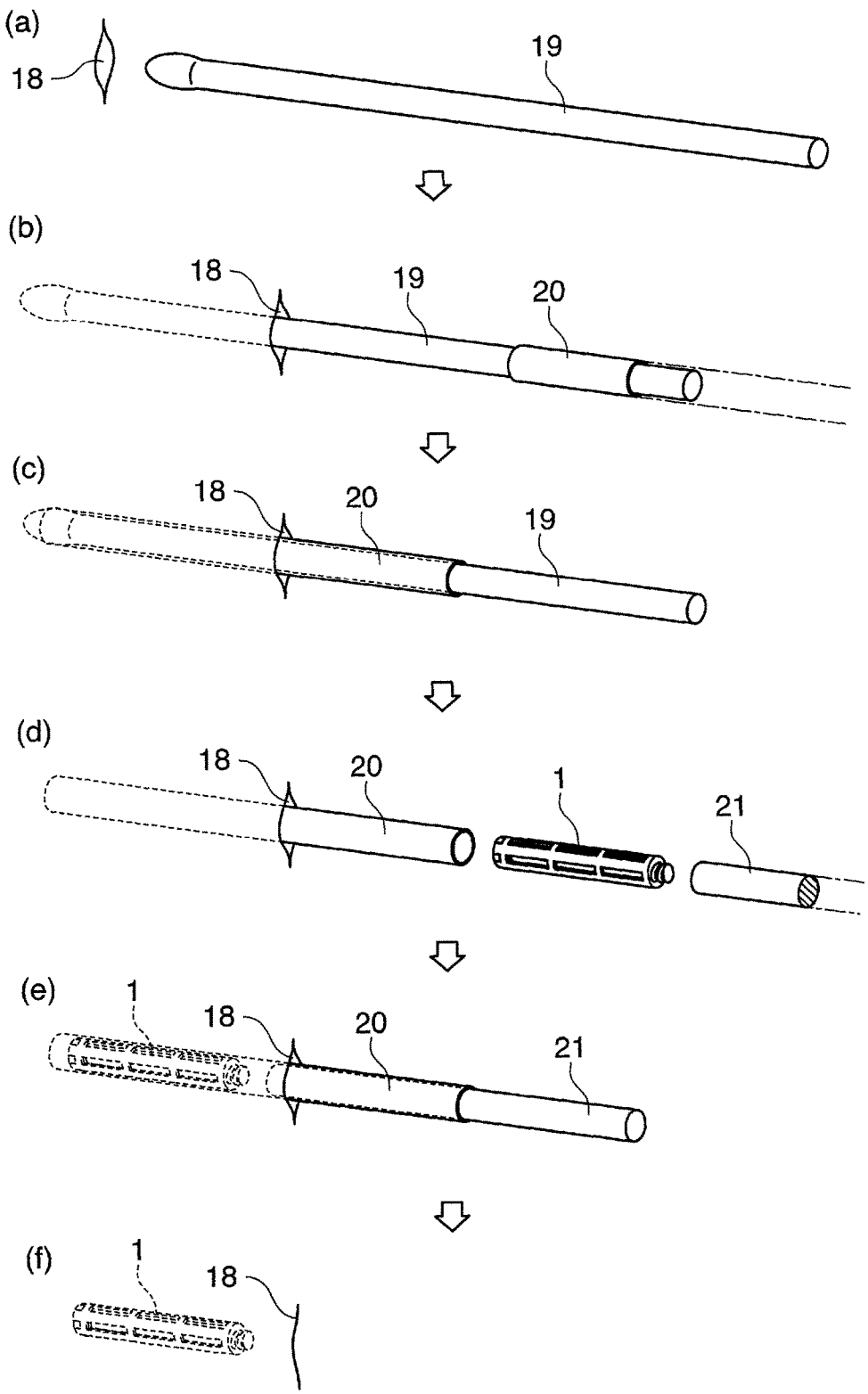
FIG. 4 is a view illustrating an installing process of a production method of the cylindrical connective tissue body.

As illustrated in FIG. 4, when the connective tissue body formation substrate 1 is to be implanted in a living body, for example, first, an insertion port 18 is formed in a surface of the living body, a distal end portion of a guide rod 19 having a distal end formed having a projecting curved shape is inserted into the living body from this insertion port 18 (FIG. 4(*a*)), and an insertion tube 20 is inserted into the living body from the insertion port 18 so that it slides on an outer side of the guide rod 19 (FIGS. 4(*b*) and 4(*c*)). Then, the connective tissue body formation substrate 1 is inserted into the insertion tube 20 (FIG. 4(*d*)) and pushed in by a pushing-in rod 21 (FIG. 4(*e*)) and then, the insertion tube 20 is withdrawn from the insertion port 18 so that the connective tissue body formation substrate 1 is installed in the living body (FIG. 4(*f*)).

<Forming Process>

After the installing process, the connective tissue 17 is formed around the connective tissue body formation substrate 1 with elapse of a predetermined time (FIGS. 3(*a*) and 3(*b*)), and moreover, the connective tissue 17 intrudes into the substrate from the slit 9, and the connective tissue 17 is formed in the connective tissue formation space 3 (FIG. 3(*b*)). In this forming process, the connective tissue 17 is formed in the tissue formation space 3 in a relatively short time by a portion of the connective tissue 17 intruded from the slit 9 with a sufficient area. The connective tissue 17 is constituted by an extracellular matrix such as a fibroblast and collagen.

<Removing Process>

After the connective tissue 17 is sufficiently formed in the tissue formation space 3 after the forming process for predetermined time, the removing process of removing the connective tissue body formation substrate 1 from the environment where the biological tissue material is present is performed (FIGS. 3(*c*) and 3(*d*)).

First, a substrate removal tool 2 for removing the connective tissue body formation substrate 1 from the environment will be described.

Figure 5:
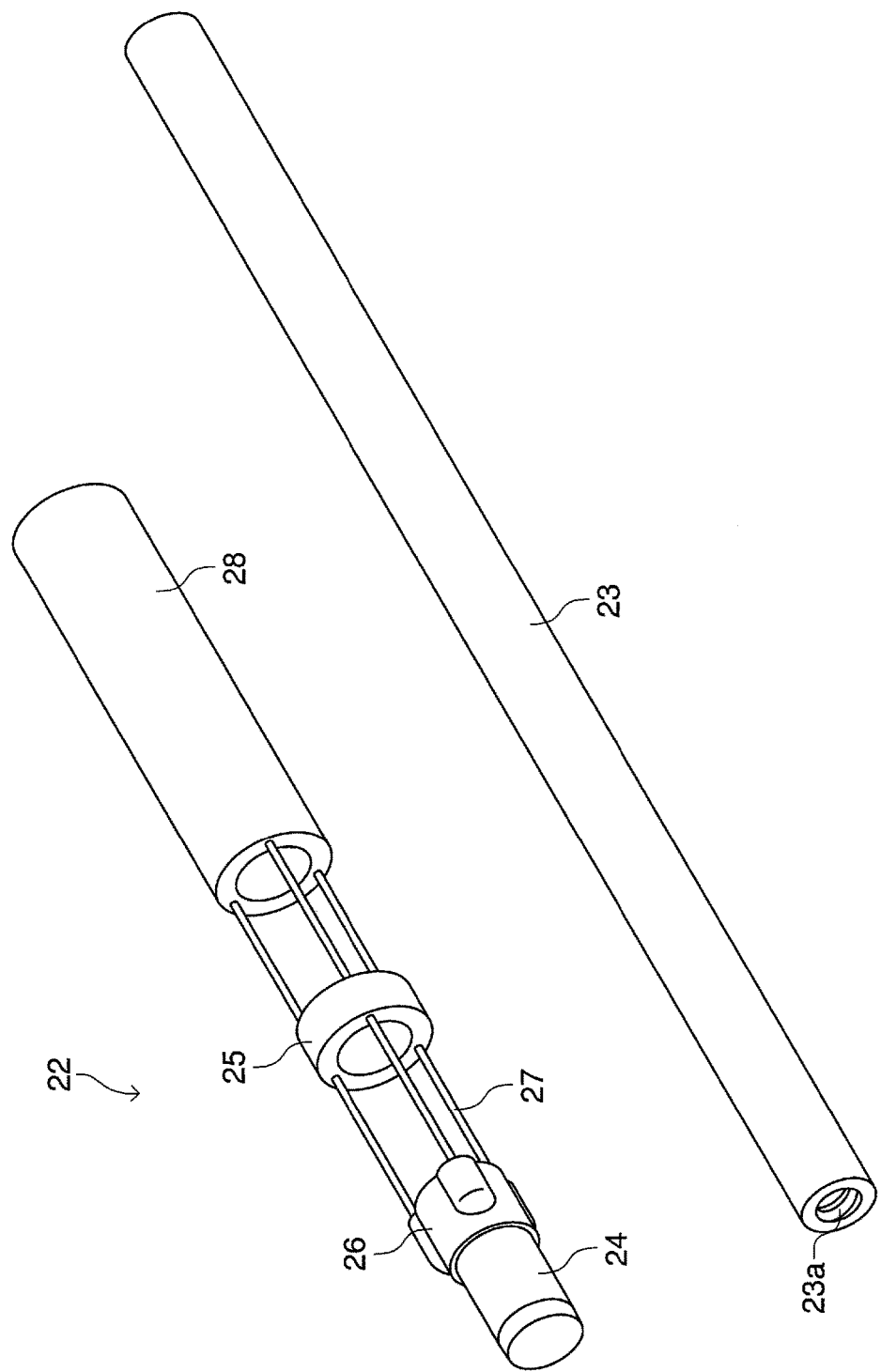
FIG. 5 is a perspective view of a substrate removal tool.

As illustrated in FIG. 5, the substrate removal tool 22 includes the aforementioned attached section 13 of the connective tissue body formation substrate 1, a fixing rod 23 for fixing the connective tissue body formation substrate 1 from an outside of the environment by being attached to the attached section 13, a cylindrical blade 24 for sliding along the outer peripheral surface of the connective tissue body formation substrate 1 and cutting out the connective tissue 17 in the periphery thereof, and a mark 25 indicating a cut-out amount targeted by the cylindrical blade 24.

The fixing rod 23 is made of an acrylic resin, for example, and has a straight rod shape having a female screw 23a formed at a distal end thereof and is constituted to be attached to the attached section 13 by screwing the female screw 23a with a screw of the attached section 13.

The cylindrical blade 24 is made of stainless, for example, and has a cylindrical shape slightly larger than the outer diameter of the connective tissue body formation substrate 1 and is constituted to cut out the connective tissue 17 around the substrate by a blade at the distal end by passing the connective tissue body formation substrate 1 therein.

A mounting ring 26 made of an acrylic resin, for example, is fixed to an outer peripheral surface on a rear part of the cylindrical blade 24, and an operation cylinder 28 made of an acrylic resin, for example, is mounted in the rear of the cylindrical blade 24 through a plurality of connecting shafts 27 made of stainless, for example.

The operation cylinder 28 has such a size that the fixing rod 23 can be inserted through a center hole of the operation cylinder 28, and by holding and pushing in the operation cylinder 28 to the distal end side in a state where the fixing rod 23 is inserted in the cylindrical blade 24 and the operation cylinder 28, the cylindrical blade 24 and the operation cylinder 28 are guided by the fixing rod 23, and the cylindrical blade 24 cuts out the connective tissue 17 around the connective tissue body formation substrate 1.

The mark 25 has a ring shape made of an acrylic resin, for example, having inner and outer diameters of the same degree as that of the cylindrical blade 24 and is made movable in a front-and-rear direction by being guided by the connecting shafts 27. By setting a position of this mark 25 as appropriate, it can be used as a mark indicating a degree of pushing-in when the connective tissue 17 around the connective tissue body formation substrate 1 is cut out by the cylindrical blade 24.

Subsequently, a procedure of removing the connective tissue body formation substrate 1 implanted in a living body, for example, by using the substrate removal tool 22 will be described.

Figure 6:
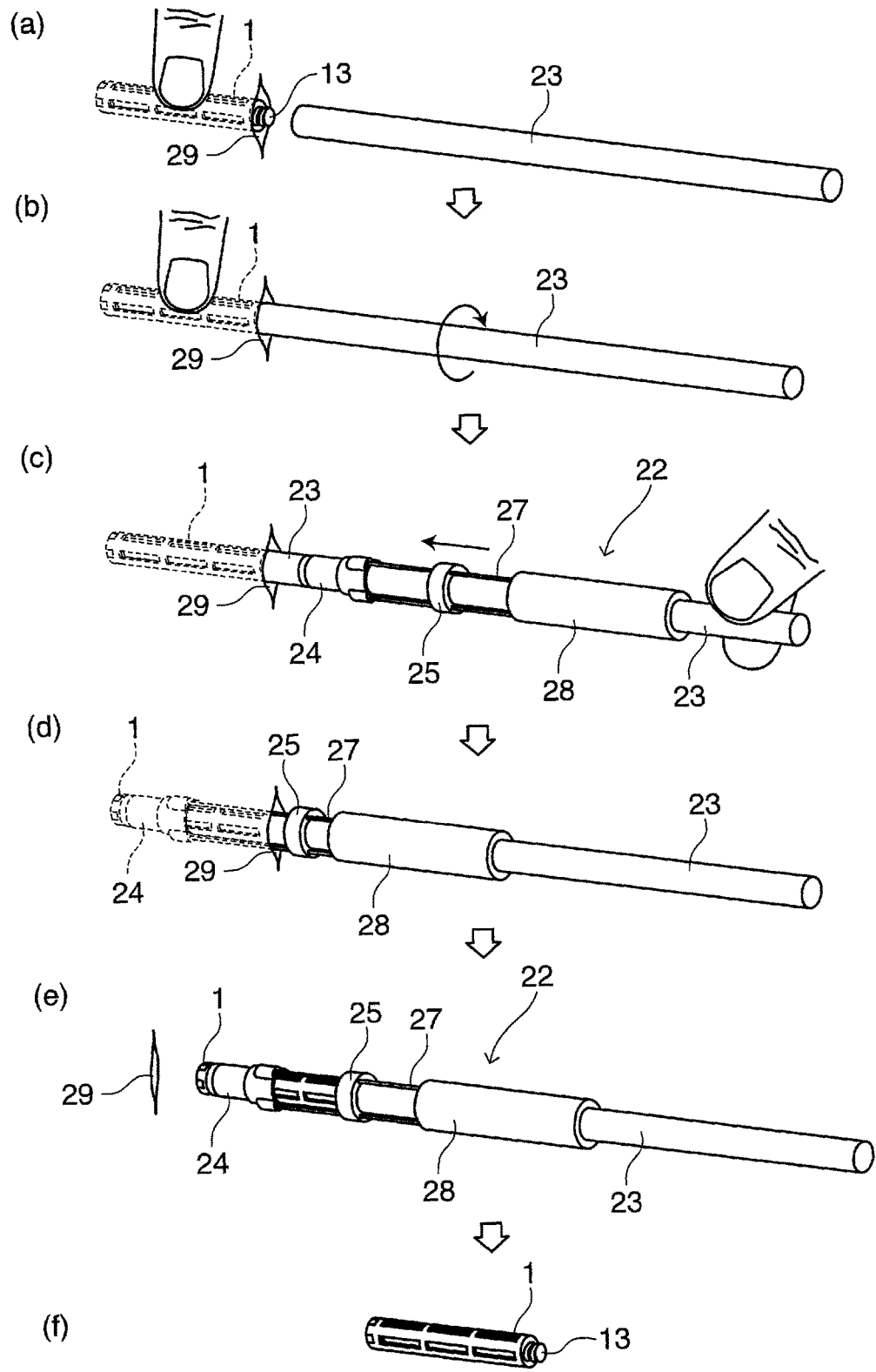
FIG. 6 is a view illustrating a removing process of the production method of the cylindrical connective tissue body.

As illustrated in FIG. 6, first, a removal port 29 is formed at a portion where the attached section 13 of the connective tissue body formation substrate 1 implanted in the living body is located in the living body surface, and the connective tissue covering the attached section 13 is removed (FIG. 6(a)).

Subsequently, the connective tissue body formation substrate 1 is held from an outer side of the living body surface, the female screw 23a at the distal end of the fixing rod 23 of the substrate removal tool 22 is screwed with the attached section 13, the fixing rod 23 is attached to the attached section 13, and the connective tissue body formation substrate 1 is fixed from the outside of the living body by the fixing rod 23 (FIGS. 6(a) and 6(b)).

The cylindrical blade 24 and the operation cylinder 28 of the substrate removal tool 22 is made to cover the fixing rod 23, a position of the mark 25 in the front-and-rear direction is adjusted, and the operation cylinder 28 is operated while the connective tissue body formation substrate 1 is fixed by holding the fixing rod 23 so that the cylindrical blade 24 and the operation cylinder 28 are pushed in toward the distal end side while being guided by the fixing rod 23 (FIG. 6(c)).

The cylindrical blade 24 and the operation cylinder 28 are pushed in until the mark 25 gets closer to the removal port 29 and movement of the cylindrical blade 24 is stopped by being regulated by the cover plate 8 of the connective tissue body formation substrate 1 as a stopper, and the connective tissue 17 in the periphery is cut out by the cylindrical blade 24 along the outer surface of the connective tissue body formation substrate 1 (FIGS. 3(c) and 6(d)).

The fixing rod 23 and the cylindrical blade 24 of the substrate removal tool 22 are withdrawn from the removal port 29 (FIG. 6(e)), and the connective tissue body formation substrate 1 is removed from the fixing rod 23 so that the connective tissue body formation substrate 1 is removed from inside the living body (FIG. 6(f)). The connective tissue 17 has been removed from the surface of the connective tissue body formation substrate 1 having been removed from inside the living body (FIG. 3(d)).

The removal procedure of the connective tissue body formation substrate 1 in which the connective tissue body formation substrate 1 is fixed by the fixing rod 23 from the outside, and the cylindrical blade 24 is guided by this fixing rod 23 so as to cut out the connective tissue 17 around the connective tissue formation substrate 1 as described here can be used as it is for removal of the connective tissue body formation substrate 1 not only from inside the living body but also from other environments where the biological tissue material is present.

<Separating Process>

By peeling the connective tissue 17 formed in the tissue formation space 3 off the tissue formation surfaces 2a and 2b and by removing it by destroying the connective tissue body formation substrate 1 as appropriate, a cylindrical connective tissue body 4 is obtained.

In the case of heteroplastic transplantation of the produced cylindrical connective tissue body 4, in order to prevent rejection after the transplantation, immune source removal treatment such as decellularization treatment, dehydration treatment and fixation treatment is preferably applied. As the decellularization treatment, a method of eluting extracellular matrix by ultrasonic treatment, surfactant treatment, enzymatic treatment such as collagenase and washing or the like can be employed, as the method of dehydration treatment, a method of washing with water-soluble organic solvent such as methanol, ethanol and isopropyl alcohol can be employed, and as the method of fixation treatment, a method of treatment with an aldehyde compound such as glutaraldehyde and formaldehyde can be employed.

Second Embodiment

Figure 7:
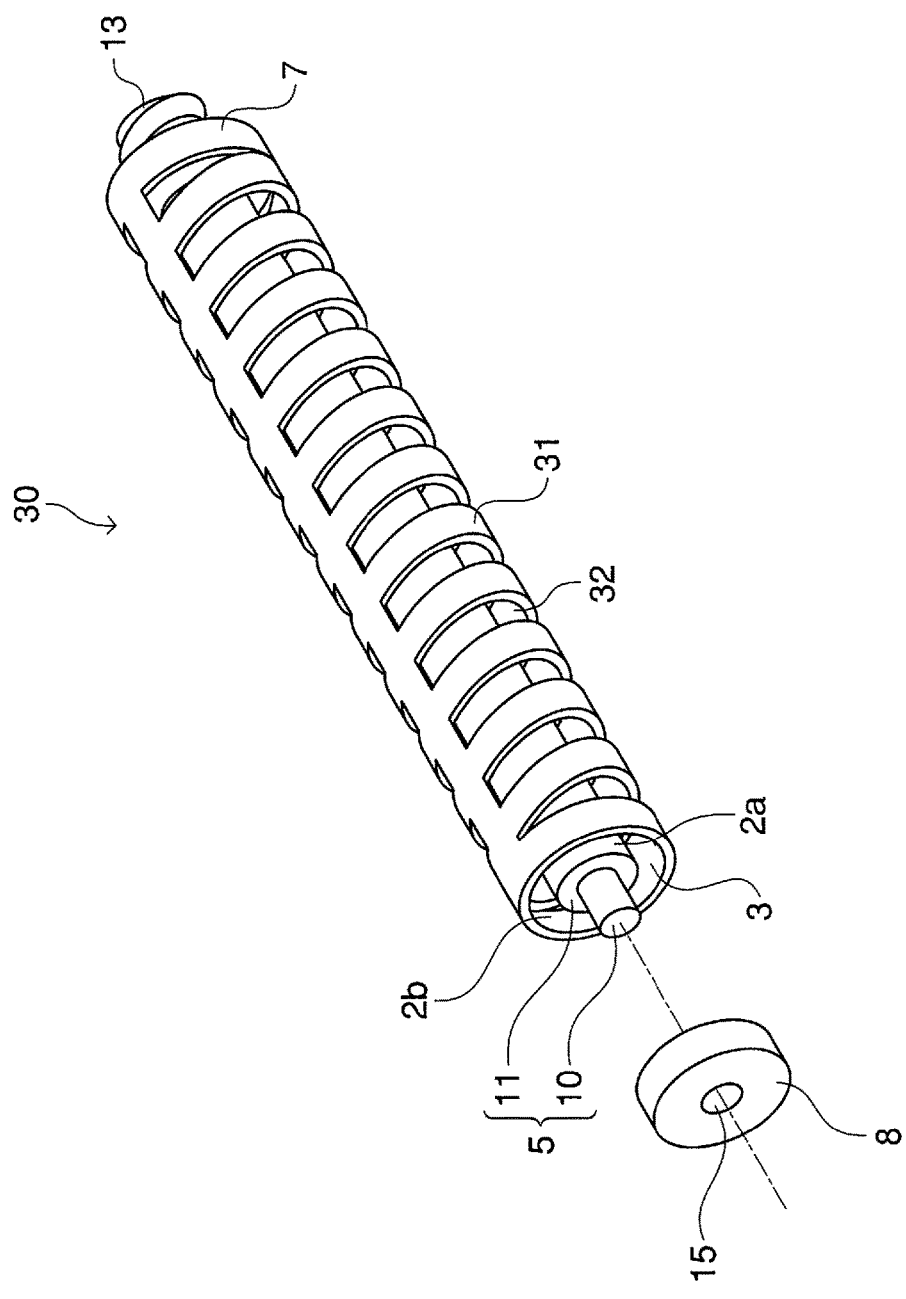
FIG. 7 is a perspective view of the connective tissue body formation substrate (second embodiment).

A second embodiment is substantially the same as the first embodiment, but as illustrated in FIG. 7, a slit 32 arranged with its longitudinal direction directed to a direction along a spiral around the substrate center axis is formed instead of the slit 9 with its longitudinal direction in parallel with the substrate center axis in the cylindrical substrate 31 of the connective tissue body formation substrate 30. As a result, a spiral rib is formed, and a structure similar to a natural blood vessel in which a tissue is constituted by a spiral fiber can be obtained. The other components are the same as those in the first embodiment.

Third Embodiment

A third embodiment is substantially the same as the first embodiment, but a connective tissue body formation substrate 34 for forming an artificial valve 33 will be described instead of the connective tissue body formation substrate 1 for forming the cylindrical connective tissue 4 used as an artificial blood vessel or the like.

Figure 8:
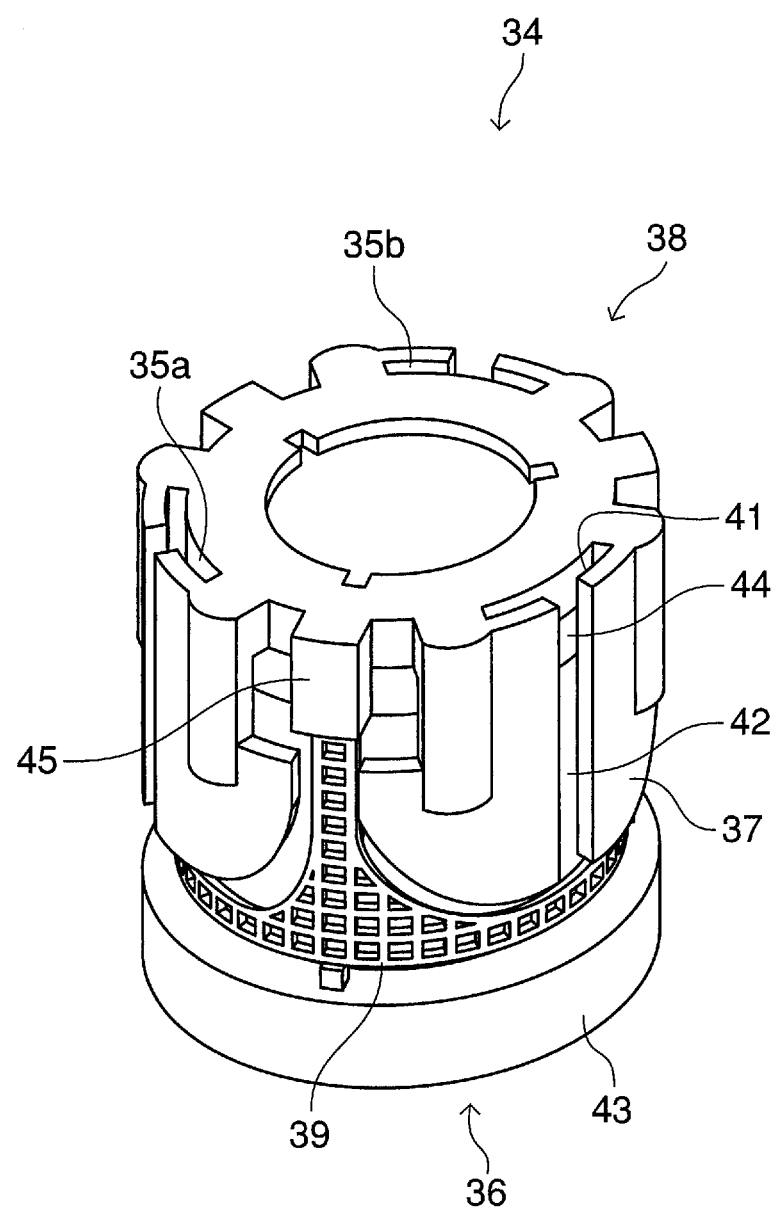
FIG. 8 is a perspective view of the connective tissue formation substrate (third embodiment).
Figure 9:
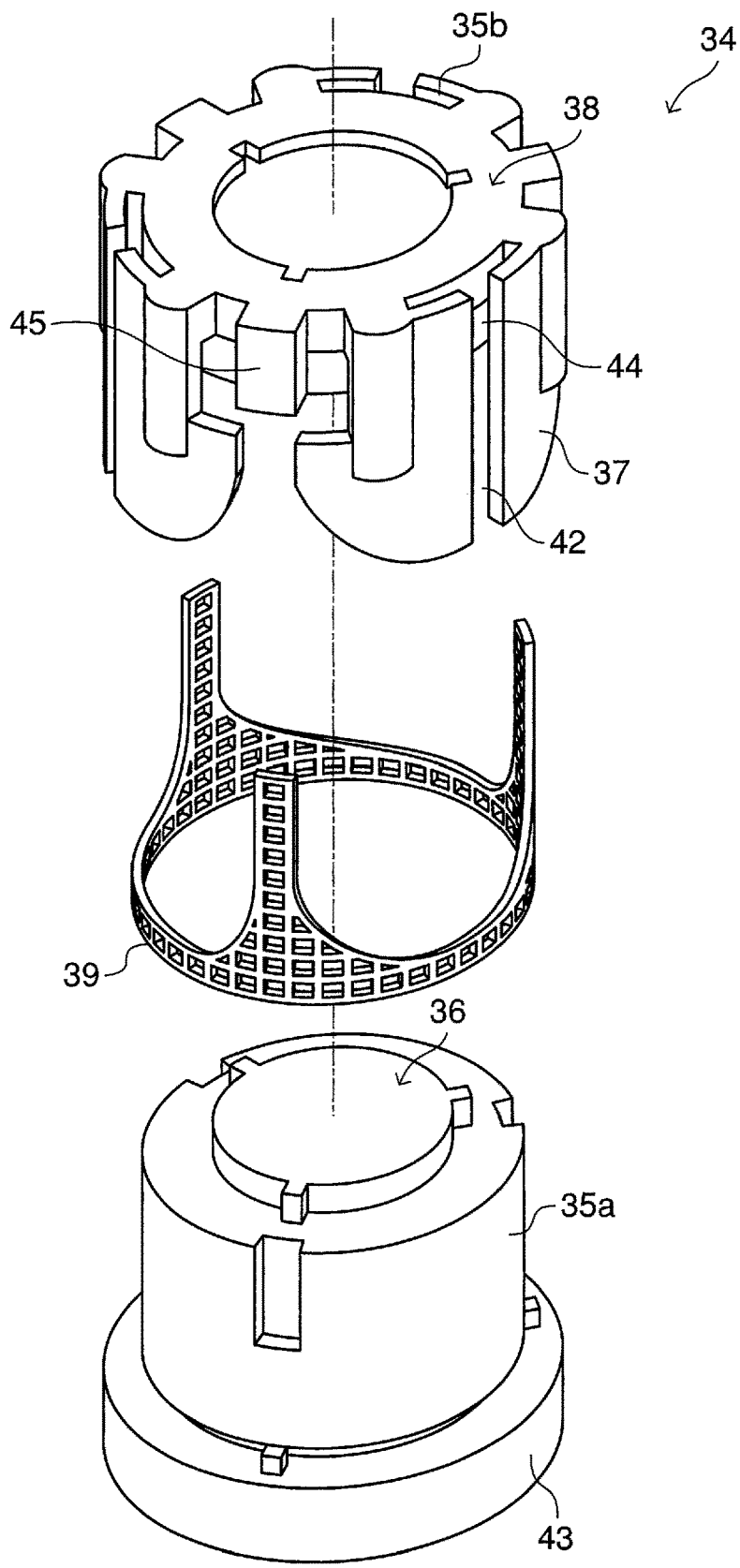
FIG. 9 is an exploded perspective view of the connective tissue body formation substrate in FIG. 8.

As illustrated in FIGS. 8 and 9, the connective tissue body formation substrate 34 includes a central substrate 36 having a tissue formation surface 35a set to an outer peripheral surface, an outer-side substrate 38 arranged on a periphery of the central substrate 36 and having a plurality of valve leaf formation sections 37 having a tissue formation surface 35b set to an inner surface, and a reinforcing material 39 for reinforcing the artificial valve 33, a space between the outer peripheral surface of the central substrate 36 and an inner surface of the valve leaf formation section 37 constitutes a tissue formation space 41 which forms a valve leaf 40, and a slit 42 is formed in the valve leaf formation section 37.

The central substrate 36 is made of an acrylic resin, for example, and has a columnar shape having a flange 43 on a lower end and has the whole surface of its outer peripheral surface set to the tissue formation surface 35a, and the valve leaf formation section 37 and the reinforcing material 39 of the outer-side substrate 38 are arranged on separate portions on an outer peripheral side thereof.

The outer-side substrate 38 is made of an acrylic resin, for example, and has a structure in which the valve leaf formation sections 37 are protruded in parallel with a center axis from a plurality of spots on the outer peripheral portion of a disk-shaped support plate 44. By attaching the support plate 44 to an upper side of the central substrate 36, the valve leaf formation section 37 is located on a part of the outer peripheral side of the central substrate 36, and its inner surface is set to the tissue formation surface 35b, while the tissue formation space 41 is formed between that and the outer peripheral surface of the central substrate 36.

The valve leaf formation section 37 is a curved plate having a substantially semi-elliptic shape having an arc at a distal end, the slit 42 is formed over the whole length at a center thereof along a center axis direction, and the connective tissue is made to intrude into the tissue formation space 41 on the back side from the slit 42.

The reinforcing material 39 is made of stainless, for example, having its cylindrical wall in a thin lattice state capable of integrating connective tissues inside and out and having a crown shape with a diameter of the same degree as that of the tissue formation space 41 and an upper edge set to have a waveform. This reinforcing material 39 is supported by inserting a distal end into a reinforcing material support section 45 formed between the valve leaf formation sections 37 in the support plate 44 and is arranged on an outer side of an exposed portion excluding a portion covered by the valve leaf formation section 37 in the outer peripheral surface of the central substrate 36.

By installing the connective tissue body formation substrate 34 in the environment where the biological tissue material is present, the portion where the reinforcing material 39 is arranged in the outer peripheral surface of the central substrate 36 is covered by the connective tissue, and the connective tissue intrudes into the tissue formation space 41 through an end-portion opening of the valve leaf formation section 37 and the slit 42. As a result, the valve leaf 40 formed in the tissue formation space 41 is set to a high quality, and the other portions are reinforced by the reinforcing material 39 at the same time.

Here, as a material of the connective tissue body formation substrate 34, similarly to the first embodiment, a resin which has such strength (hardness) that is not largely deformed when being implanted into a living body, chemical stability, resistance against a load such as disinfection and has no or little effluent which stimulates a living body is preferable, and an acrylic resin and the like as described above can be cited, for example, but it is not limiting.

For example, as described above, at least an outer peripheral surface of the central substrate 36 can be formed by a polymer material such as an acrylic resin on which the connective tissue can be formed relatively easily and then, at least a surface of the valve leaf formation section 37 of the outer-side substrate 38 can be formed by a metal material on which the connective tissue is not formed relatively easily. As a result, closure of the slit 42 by the connective tissue can be delayed while the connective tissue is formed in the tissue formation space 41.

Figure 10:
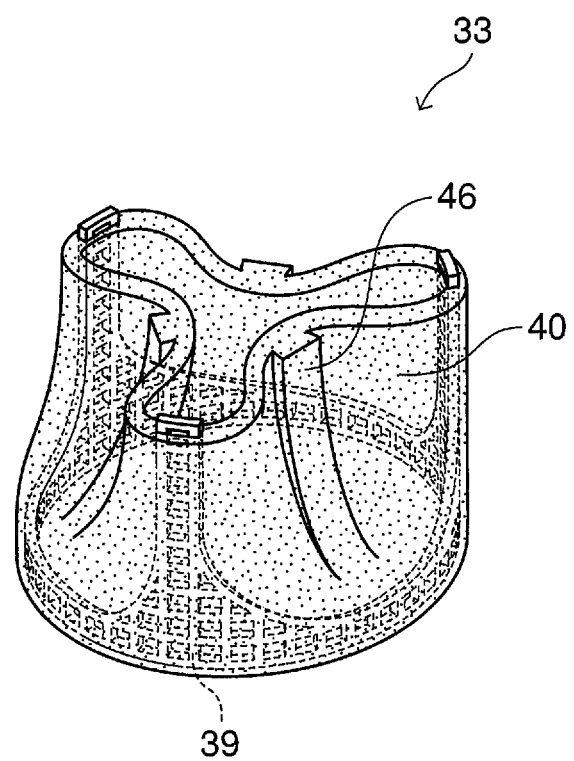
FIG. 10 is a perspective view of an artificial valve.

As illustrated in FIG. 10, for example, the artificial valve 33 is to give a valve function by being transplanted in a blood vessel such as an aorta from a heart and is constituted to open/close a flow passage inside by displacement of the plurality of valve leaves 40 inward and outward by a pressure of a fluid flowing therein.

The valve leaf 40 is a portion repeatedly displaced but is set to a high quality by forming both inner and outer surfaces conforming to the tissue formation surfaces 35*a* and 35*b* and is reinforced by a rib 46 formed at a portion corresponding to the slit 42.

The portion excluding the valve leaf 40 is reinforced by the reinforcing material 39 so that the shape of the artificial valve 33 can be held easily, strength and rigidity of a sutured portion of the artificial valve 33 are improved, and the suture of the artificial valve 33 to the heart or the blood vessel is facilitated.

Though the other components are the same as those in the first embodiment, a change may be added as appropriate such that the connective tissues connected inside and out of the slit 42 are cut out individually by the cutting blade so as to remove the connective tissue body formation substrate 34 without using the substrate removal tool in the removing process, for example.

Fourth Embodiment

Figure 11:
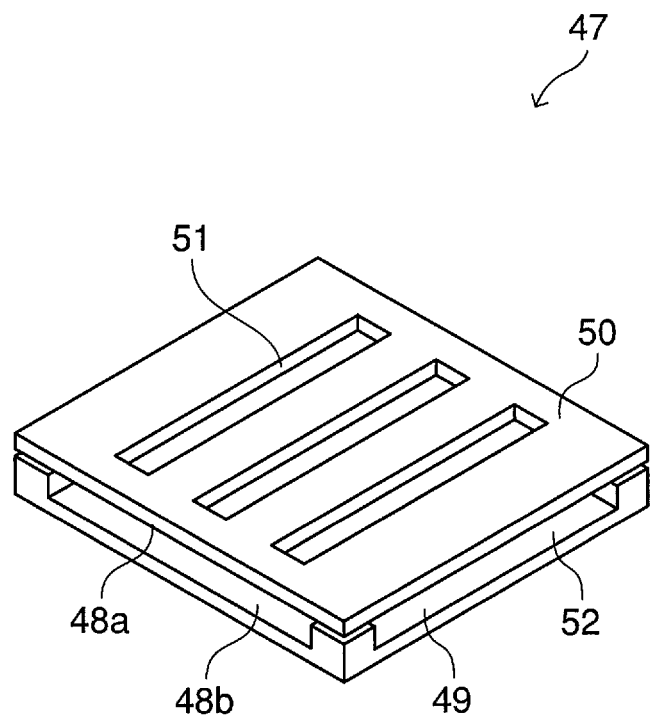
FIG. 11 is a perspective view of the connective tissue body formation substrate (fourth embodiment).

A fourth embodiment is substantially the same as the first embodiment, but as illustrated in FIG. 11, a substrate of this embodiment is a connective tissue body formation substrate 47 for forming a plate-shaped connective tissue body in which two plate-shaped substrates 49 and 50 having tissue formation surfaces 48*a* and 48*b* are provided at an interval from each other, and a slit 51 is formed in both of the two plate-shaped substrates 49 and 50. As a result, the connective tissue can be easily made to intrude from the slits 51 formed in the plate-shaped substrates 49 and 50, and a plate-shaped connective tissue body can be formed in a tissue formation space 52 between the plate-shaped substrates 49 and 50.

Here, as a material of the connective tissue body formation substrate 47, similarly to the first embodiment, a resin which has such strength (hardness) that is not largely deformed when being implanted into a living body, chemical stability, resistance against a load such as disinfection and has no or little effluent which stimulates a living body is preferable, and an acrylic resin and the like can be cited, for example, but it is not limiting.

The slit 51 can be formed not only in both the two plate-shaped substrates 49 and 50 but can be formed only in the plate-shaped substrate 50, which is one of the two. In this case, at least a surface of the plate-shaped substrate 49 not having the slit 51 is formed by a polymer material such as an acrylic resin on which the connective tissue can be formed relatively easily and then, at least the surface of the plate-shaped substrate 50 having the slit 51 can be formed by a metal material on which the connective tissue is not formed relatively easily. As a result, closure of the slit 51 by the connective tissue can be delayed while the connective tissue is formed in the tissue formation space 52.

Moreover, though the other components are the same as those of the first embodiment, a change may be added as appropriate such that the connective tissues connected inside and out of the slit 51 are cut out individually by the cutting blade so as to remove the connective tissue body formation substrate 47 without using the substrate removal tool in the removing process, for example.

Fifth Embodiment

Figure 12:
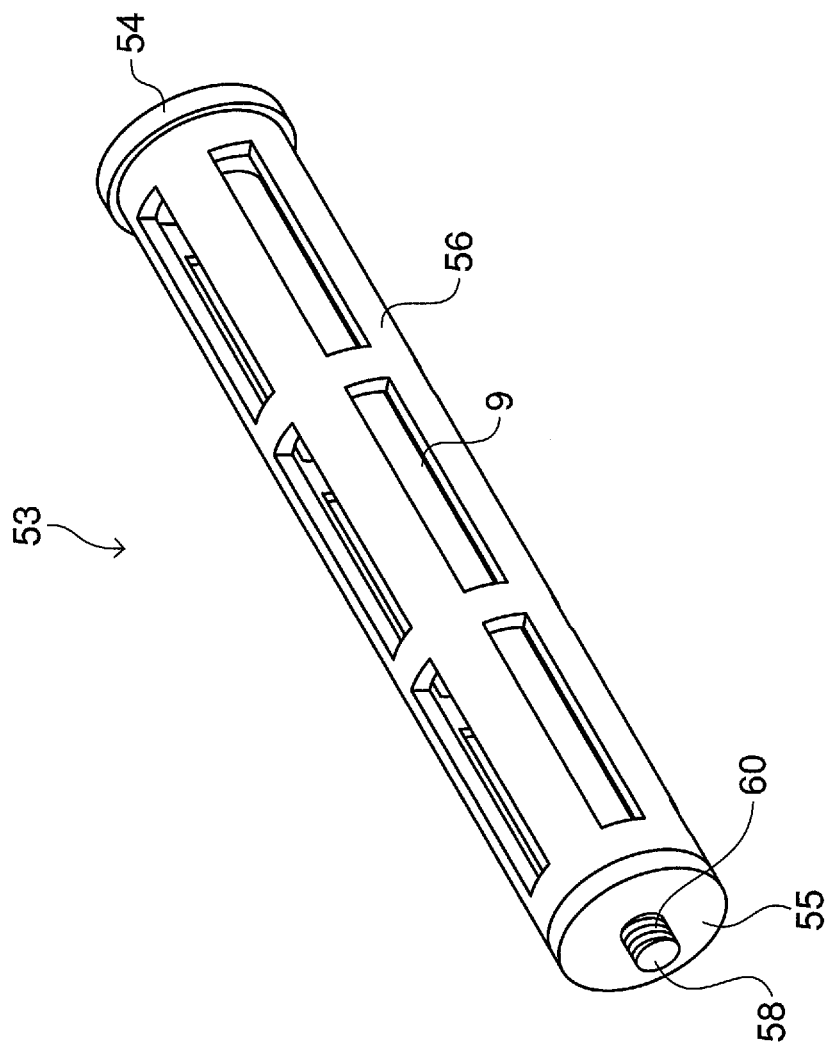
FIG. 12 is a perspective view of the connective tissue body formation substrate (fifth embodiment).
Figure 13:
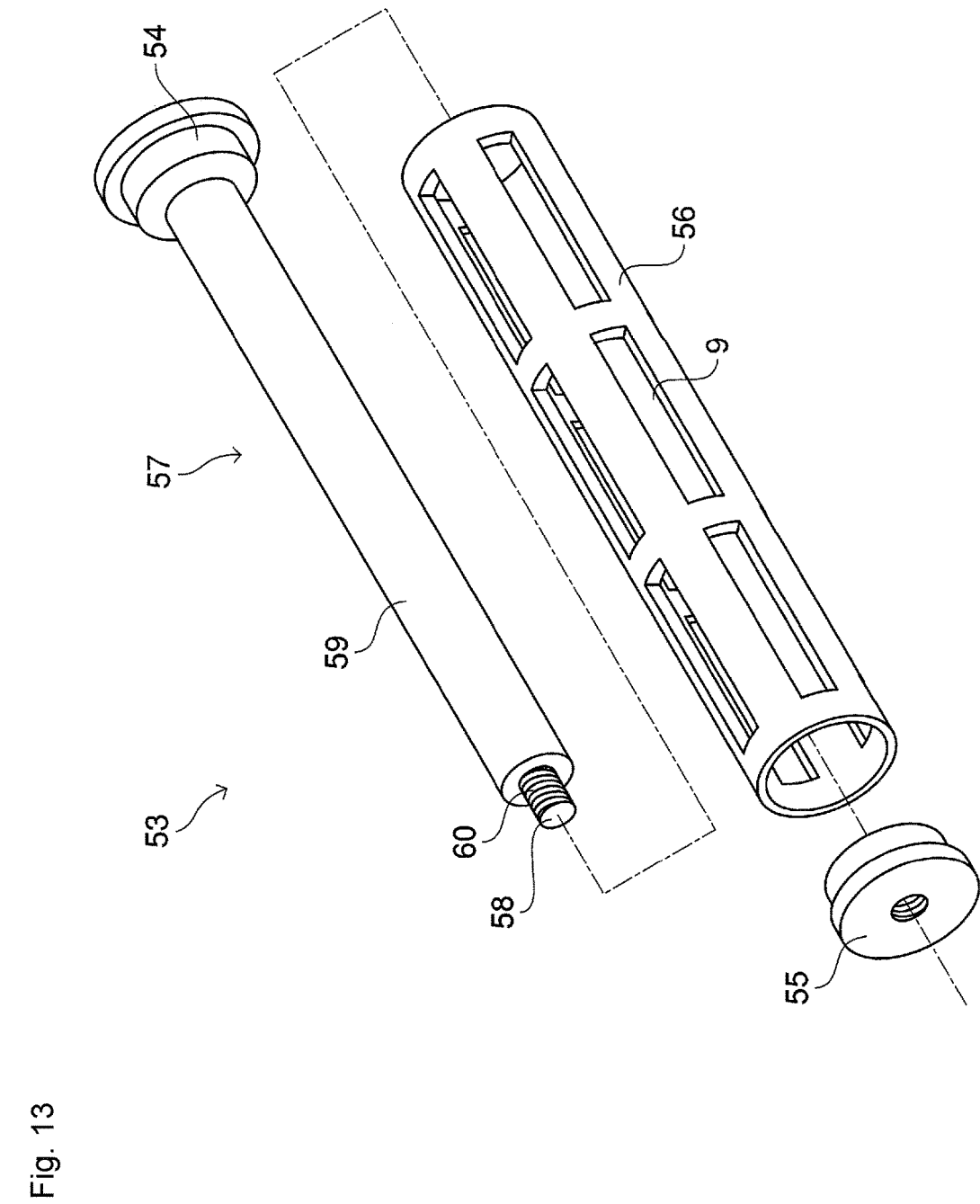
FIG. 13 is an exploded perspective view of the connective tissue body formation substrate in FIG. 12.

A fifth embodiment is substantially the same as the first embodiment, but as illustrated in FIGS. 12 and 13, a connective tissue body formation substrate 53 of this embodiment is assembled by forming an end plate 54 and a cover plate 55 separately from a cylindrical substrate 56 and by internally fitting the end plate 54 and the cover plate 55 in an end portion of the cylindrical substrate 56 while leaving flanges on outer ends thereof, while a central substrate 57 is passed through the cylindrical substrate 56.

The central substrate 57 has a structure in which a cover tube 59 covers a periphery of the central material 58 protruding from a center of the end plate 54 similarly to the first embodiment, and a screw 60 is formed at a distal end part exposed from the cover tube 59 in the central material 58, and the cover plate 55 is screwed with this screw 60. The screw 60 protrudes from the cover plate 55 in a state where the connective tissue body formation substrate 53 is assembled, and this protruding portion functions as an attached section to be attached to the fixing rod 23 of the substrate removal tool 22.

Here, the connective tissue body formation substrate 53 has a structure assembled by screwing the cover plate 55 with the screw 60, and a metal material is suitably used for its material, but a silicone resin and an acrylic resin or the like can be also employed similarly to the first embodiment.

When a metal material is used for the connective tissue body formation substrate 53, by forming the end plate 54, the cylindrical substrate 56, the central material 58, and the cover plate 60 by the metal material exemplified in the first embodiment and by forming the cover tube 59 by a polymer material such as a silicone resin, closure of the slit 9 by the connective tissue can be delayed while the connective tissue is formed in the tissue formation space. The other components are the same as those in the first embodiment.

Sixth Embodiment

Figure 14:
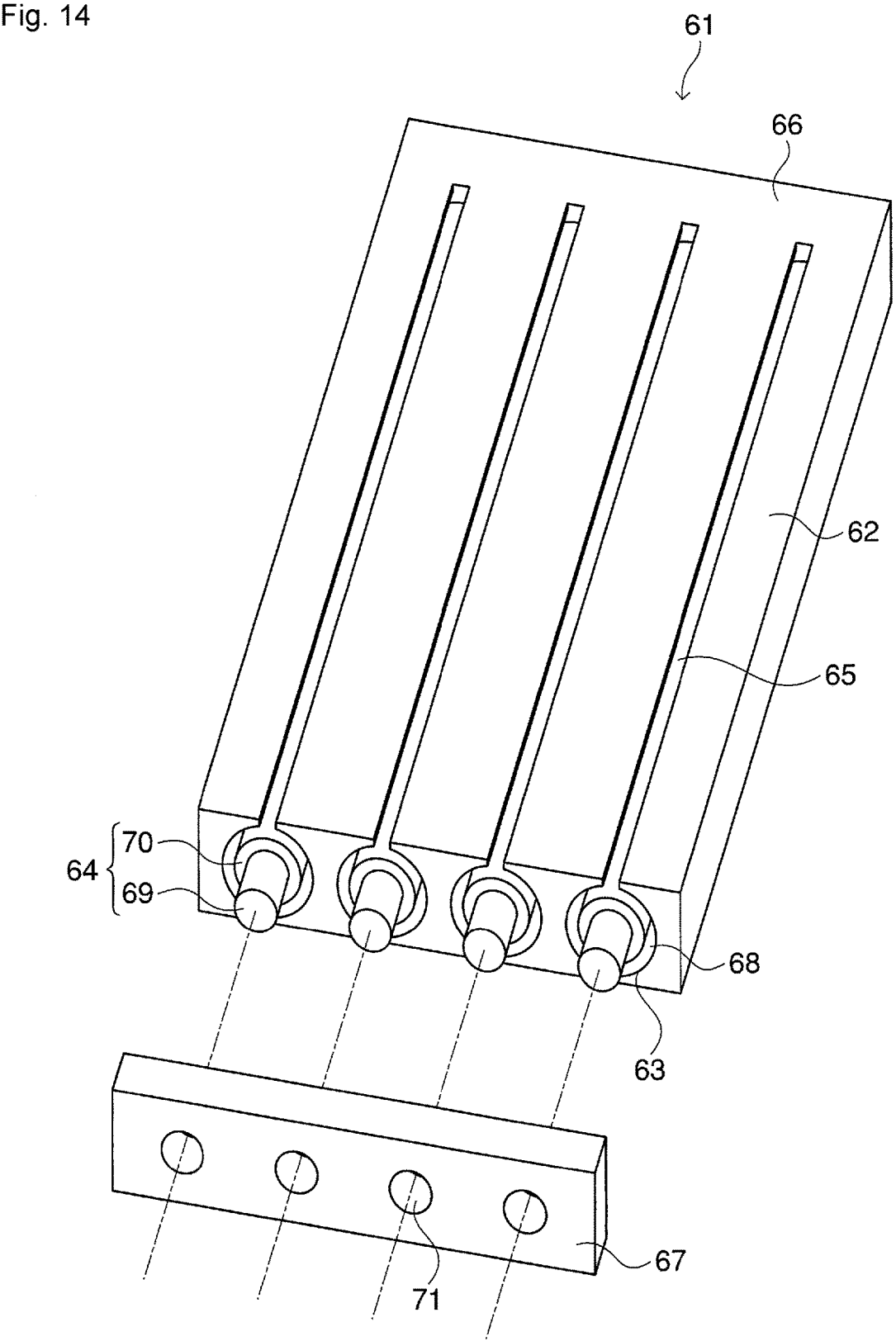
FIG. 14 is a perspective view of the connective tissue body formation substrate (sixth embodiment).

A sixth embodiment is substantially the same as the first embodiment, but as illustrated in FIG. 14, in a connective tissue body formation substrate 61 of this embodiment, a rectangular and thick plate-shaped accommodating substrate 62 made of an acrylic resin, for example, is provided instead of the cylindrical substrate 6, a plurality of accommodating sections 63 is formed in this accommodating substrate 62, a central substrate 64 is accommodated in each of the accommodating sections 63, and a plurality of slits 65 allowing each of the accommodating sections 63 and the outside of the substrate to communicate with each other is formed in the accommodating substrate 62, and a plurality of the cylindrical connective tissue bodies is are formed at the same time.

The accommodating section 63 is a space having a substantially circular section with its inner peripheral surface as a tissue formation surface, a plurality of the accommodating sections 63 are formed in parallel with a long side of the accommodating substrate 62 by leaving the end plate 66 set to one end side of the accommodating substrate 62, and openings on the other end sides of the plurality of accommodating sections 63 are closed by a cover plate 67 set to the same outer shape as the section of the accommodating substrate 62 and made of an acrylic resin, for example. The slit 65 allowing each of the accommodating sections 63 to communicate with the outside of the substrate is formed over the whole length of each of the accommodating sections 63 in parallel with its center axis so that the connective tissue intrudes into a tissue formation space 68 between the accommodating section 63 and the central substrate 64.

The central substrate 64 has a structure in which a cover tube 70 made of a silicone resin, for example, covers a periphery of a central material 69 made of an acrylic resin, for example, protruding from a center of the end plate 66 similarly to the first embodiment, and an outer peripheral surface of the cover tube 70 is set to a tissue formation surface. A distal end portion of the central material 69 is exposed from the cover tube 70 and is also protruded from the accommodating section 63, and the cover plate 67 is attached to the accommodating substrate 62 by fitting a plurality of small holes 71 of the cover plate 67 with the protruding portions of the plurality of central materials 69.

Here, as a material of the connective tissue body formation substrate 61, similarly to the first embodiment, a resin which has such strength (hardness) that is not largely deformed when being implanted into a living body, chemical stability, resistance against a load such as disinfection and has no or little effluent which stimulates a living body is preferable, and an acrylic resin, a silicone resin and the like can be cited, for example, as described above, but it is not limiting.

For example, as described above, at least an outer peripheral surface of the central substrate 64 can be formed by a polymer material such as a silicone resin on which the connective tissue can be formed relatively easily and then, at least a surface of the accommodating substrate 62 can be formed by a metal material on which the connective tissue is not formed relatively easily. As a result, closure of the slit 65 by the connective tissue can be delayed while the connective tissue is formed in the tissue formation space 68.

According to the constitution of this embodiment, since the plurality of cylindrical connective tissues body is formed by one connective tissue body formation substrate 61 at the same time, the number of times of the installing process and the removing process when a large number of the cylindrical connective tissue bodies are formed can be reduced, and a burden on the environment where the connective tissue body formation substrate 61 is installed can be reduced.

Moreover, even if an extremely small cylindrical connective tissue body having an outer diameter of approximately 2 mm or less and an inner diameter of approximately 1 mm or less, for example, is to be formed, since the plurality of cylindrical connective tissue bodies are is formed at the same time, the connective tissue body formation substrate 61 becomes a certain size. As a result, in the removing process, in the environment where the connective tissue body formation substrate 61 is installed, the connective tissue body formation substrate 61 can be easily found. The other components are the same as those in the first embodiment.

REFERENCE SIGNS LIST 1 connective tissue body formation substrate (first embodiment)
2a, 2b tissue formation surface
3 tissue formation space
4 cylindrical connective tissue body
5 central substrate
6 cylindrical substrate
7 end plate
8 cover plate
9 slit
10 central material
11 cover tube
12 notch
13 attached section
14 projecting section
15 small hole
16 rib
17 connective tissue
18 insertion port
19 guide rod
20 insertion tube
21 pushing-in rod
22 substrate removal tool
23 fixing rod
23a female screw
24 cylindrical blade
25 mark
26 mounting ring
27 connecting shaft
28 operation cylinder
29 removal port
30 connective tissue body formation substrate (second embodiment)
31 cylindrical substrate
32 slit
33 artificial valve
34 connective tissue body formation substrate (third embodiment)
35a, 35b tissue formation surface
36 central substrate
37 valve leaf formation section
38 outer-side substrate
39 reinforcing material
40 valve leaf 41 tissue formation space
42 slit
43 flange
44 support plate
45 reinforcing material support section
46 rib
47 connective tissue body formation substrate (fourth embodiment)
48a, 48b tissue formation surface
49, 50 plate-shaped substrate
51 slit
52 tissue formation space
53 connective tissue formation substrate (fifth embodiment)
54 end plate
55 cover plate
56 cylindrical substrate
57 central substrate
58 central material
59 cover tube
60 screw
61 connective tissue body formation substrate (sixth embodiment)
62 accommodating substrate
63 accommodating section
64 central substrate
65 slit
66 end plate
67 cover plate
68 tissue formation space
69 central material
70 cover tube
71 small hole

The invention claimed is:

1. A method of producing a film connective tissue body using a connective tissue body formation substrate comprising two tissue formation surfaces facing each other with a tissue formation space interposed therebetween and a slit at least in one of the tissue formation surfaces, the method comprising:
an installing process of installing the connective tissue body formation substrate comprising two tissue formation surfaces facing each other with a tissue formation space interposed therebetween and a slit at least in one of the tissue formation surfaces in an environment where a biological tissue material is present,
a forming process of forming a connective tissue in the tissue formation space while the connective tissue is formed around the connective tissue body formation substrate,
a removing process of removing the connective tissue body formation substrate from the environment, wherein the connective tissue body formation substrate is fixed, and the connective tissue in a periphery is cut out along an outer surface of the connective tissue body formation substrate and then the connective tissue body formation substrate is removed, and
a separating process of peeling the connective tissue in the tissue formation space off the tissue formation surface and removing the connective tissue as a film connective tissue.

2. The method according to claim 1, wherein a ratio of an area of the slit to the tissue formation surface is set to ½ or less.

3. The method according to claim 1, wherein the connective tissue body formation substrate further comprises a central substrate having the tissue formation surface set to an outer peripheral surface and a cylindrical substrate surrounding the central substrate and having the tissue formation surface set to an inner peripheral surface, and the slit is formed in the cylindrical substrate.

4. The method according to claim 3, wherein at least an outer peripheral surface of the central substrate is formed of a polymer material, and at least a surface of the cylindrical substrate is formed of a metal material.

5. The method according to claim 3, wherein the slit is arranged with its longitudinal direction toward a direction in parallel with a substrate center axis.

6. The method according to claim 3, wherein the slit is arranged with its longitudinal direction toward a direction along a spiral around a substrate center axis.

7. The method according to claim 1, wherein the connective tissue body formation substrate further comprises a plurality of central substrates each having the tissue formation surface set to an outer peripheral surface and an accommodating substrate having a plurality of accommodating sections each accommodating the central substrate and having the tissue formation surface set to an inner peripheral surface, and the slit is formed in the accommodating substrate.

8. The method according to claim 7, wherein at least the outer peripheral surface of the central substrate is formed of a polymer material, and at least a surface of the accommodating substrate is formed of a metal material.

9. The method according to claim 1, wherein the connective tissue body formation substrate further comprises a central substrate having the tissue formation surface set to an outer peripheral surface and outer substrates arranged around the central substrate and having a plurality of valve leaf formation sections each having the tissue formation surface set to an inner surface, and the slit is formed in the valve leaf formation section of the outer substrate.

10. The method according to claim 9, wherein at least the outer peripheral surface of the central substrate is formed of a polymer material, and at least a surface of the valve leaf formation section is formed of a metal material.

11. The method according to claim 9, wherein a reinforcing material for reinforcing the connective tissue is arranged on an outer side of an exposed portion excluding a portion covered by the valve leaf formation section in the outer peripheral surface of the central substrate.

12. The method according to claim 1, wherein the connective tissue body formation substrate further comprises two plate-shaped substrates each having the tissue formation surface at an interval from each other, and the slit is formed at least in one of the two plate-shaped substrates.

13. The method according to claim 12, wherein the slit is formed only in one of the two plate-shaped substrates, at least a surface of the plate-shaped substrate not having the slit is formed of a polymer material, and at least a surface of the plate-shaped substrate having the slit is formed of a metal material.

* * * * *